United States Patent
Baril

(10) Patent No.: US 10,912,545 B2
(45) Date of Patent: Feb. 9, 2021

(54) TISSUE SPECIMEN RETRIEVAL DEVICES AND METHODS

(71) Applicant: COVIDIEN LP, Mansfield, MA (US)

(72) Inventor: Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 192 days.

(21) Appl. No.: 16/266,264

(22) Filed: Feb. 4, 2019

(65) Prior Publication Data

US 2020/0245988 A1 Aug. 6, 2020

(51) Int. Cl.
*A61B 17/00* (2006.01)

(52) U.S. Cl.
CPC ............... *A61B 17/00234* (2013.01); *A61B 2017/00287* (2013.01); *A61B 2017/00314* (2013.01); *A61B 2017/00862* (2013.01)

(58) Field of Classification Search
CPC ............ A61B 17/00234; A61B 17/221; A61B 17/32056; A61B 17/0218; A61B 17/22031; A61B 17/29; A61B 2017/00287; A61B 2017/00314; A61B 2017/00367; A61B 2017/00862; A61B 2017/2212; A61B 2017/00867; A61B 2017/2215; A61B 2017/2927; A61B 2017/320064; A61B 2018/1407; A61B 2018/141; A61B 18/1492; A61B 10/02; A61F 5/0089; A61F 9/00709

See application file for complete search history.

(56) References Cited

U.S. PATENT DOCUMENTS

| | | | |
|---|---|---|---|
| 5,354,303 A | * | 10/1994 | Spaeth ............. A61B 17/00234 604/171 |
| 6,059,793 A | | 5/2000 | Pagedas |
| 6,156,055 A | | 12/2000 | Ravenscroft |
| 6,162,209 A | | 12/2000 | Gobron et al. |
| 6,171,317 B1 | | 1/2001 | Jackson et al. |
| 6,206,889 B1 | | 3/2001 | Bennardo |
| 6,224,612 B1 | | 5/2001 | Bates et al. |
| 6,228,095 B1 | | 5/2001 | Dennis |
| 6,248,113 B1 | | 6/2001 | Fina |
| 6,258,102 B1 | | 7/2001 | Pagedas |
| 6,264,663 B1 | | 7/2001 | Cano |
| 6,270,505 B1 | | 8/2001 | Yoshida et al. |
| 6,280,451 B1 | | 8/2001 | Bates et al. |
| 6,344,026 B1 | | 2/2002 | Burbank et al. |
| 6,350,266 B1 | | 2/2002 | White et al. |

(Continued)

*Primary Examiner* — Mohamed G Gabr

(74) *Attorney, Agent, or Firm* — Carter, DeLuca & Farrell LLP

(57) ABSTRACT

A tissue specimen retrieval device includes an end effector assembly including first and second arms including respective first and second proximal segments and respective first and second distal segments. The first and second distal segments each include first and second end portions. First and second joints operable couple the first and second end portions of the first and second distal segments, respectively. A third joint operably couples the first proximal and first distal segments and a fourth joint operably couples the second proximal and distal segments. The first and second distal segments are movable relative to one another about the first and second joints. The first and second distal segments are movable relative to the first and second proximal segments about the third and fourth joints.

20 Claims, 4 Drawing Sheets

(56) References Cited

U.S. PATENT DOCUMENTS

| | | |
|---|---|---|
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2008/0221588 A1* | 9/2008 | Hollis .............. A61B 17/00234 606/114 |
| 2008/0234696 A1* | 9/2008 | Taylor .............. A61B 17/00234 606/114 |
| 2011/0184430 A1* | 7/2011 | Parihar ............ A61B 17/00234 606/114 |

* cited by examiner

TISSUE SPECIMEN RETRIEVAL DEVICES AND METHODS

BACKGROUND

Technical Field

The present disclosure relates to tissue specimen retrieval from an internal body cavity and, more particularly, to tissue specimen retrieval devices and methods to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue specimen retrieval device including an end effector assembly having first and second arms. The first arm includes a first proximal segment and a first distal segment. The first distal segment includes first and second end portions. The second arm includes a second proximal segment and a second distal segment. The second distal segment includes first and second end portions. A first joint operably couples the first end portions of the first and second distal segments. A second joint operably couples the second end portions of the first and second distal segments. A third joint operably couples the first proximal and first distal segments. A fourth joint operably couples the second proximal and distal segments. The first and second distal segments are movable relative to one another about the first and second joints and the first and second distal segments are movable relative to the first and second proximal segments about the third and fourth joints.

In an aspect of the present disclosure, the end effector assembly further includes a tissue specimen bag supported on the first and second distal segments.

In another aspect of the present disclosure, the first and second proximal segments are substantially co-planar to thereby define a first plane and the first and second distal segments are substantially co-planar to thereby define a second plane.

In another aspect of the present disclosure, movement of the first and second distal segments relative to the first and second proximal segments about the third and fourth joints moves the first and second planes relative to one another.

In still another aspect of the present disclosure, the first and second proximal segments are configured to flex relative to one another. In such aspects, the first and second planes may remain relatively stationary during flexion of the first and second proximal segments relative to one another.

In yet another aspect of the present disclosure, the first and second planes remain relatively stationary during movement of the first and second distal segments relative to one another about the first and second joints.

In still yet another aspect of the present disclosure, at least one of the first, second, third, or fourth joints includes a torsion spring. In such aspects, the torsion spring may include a body and first and second legs extending from the body. The first and second legs are configured to engage first and second tube portions such that movement of the first and second tube portions relative to one another tensions or un-tensions the body.

A tissue specimen retrieval device provided in accordance with aspects of the present disclosure includes a first shaft and a second shaft telescopically movable relative to the first shaft. The second shaft supports an end effector assembly at a distal end portion thereof and is movable relative to the first shaft between a retracted position, wherein the end effector assembly is disposed within the first shaft, and a deployed position, wherein the end effector assembly extends distally from the first shaft. The end effector assembly may be configured similar to any of the aspects detailed above or otherwise herein.

In an aspect of the present disclosure, a first handle is disposed at a proximal end portion of the first shaft and a second handle is disposed at a proximal end portion of the second handle. In such aspects, the first and second handles are relatively movable to move the second shaft between the retracted and deployed positions.

In another aspect of the present disclosure, a tissue specimen bag is supported on the first and second distal segments. In such aspects, in the retracted position, the tissue specimen bag is disposed within the first shaft.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
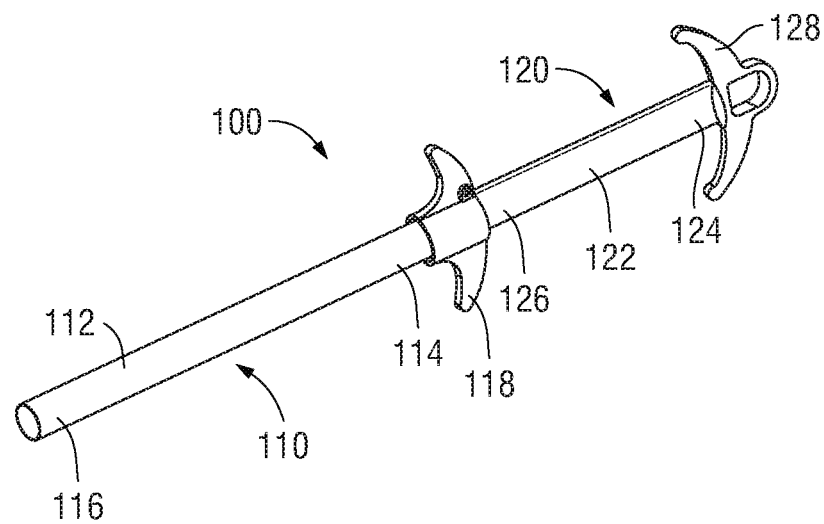
FIG. 1 is a perspective view of a tissue specimen retrieval device provided in accordance with aspects of the present disclosure, disposed in a retracted position.
Figure 2:
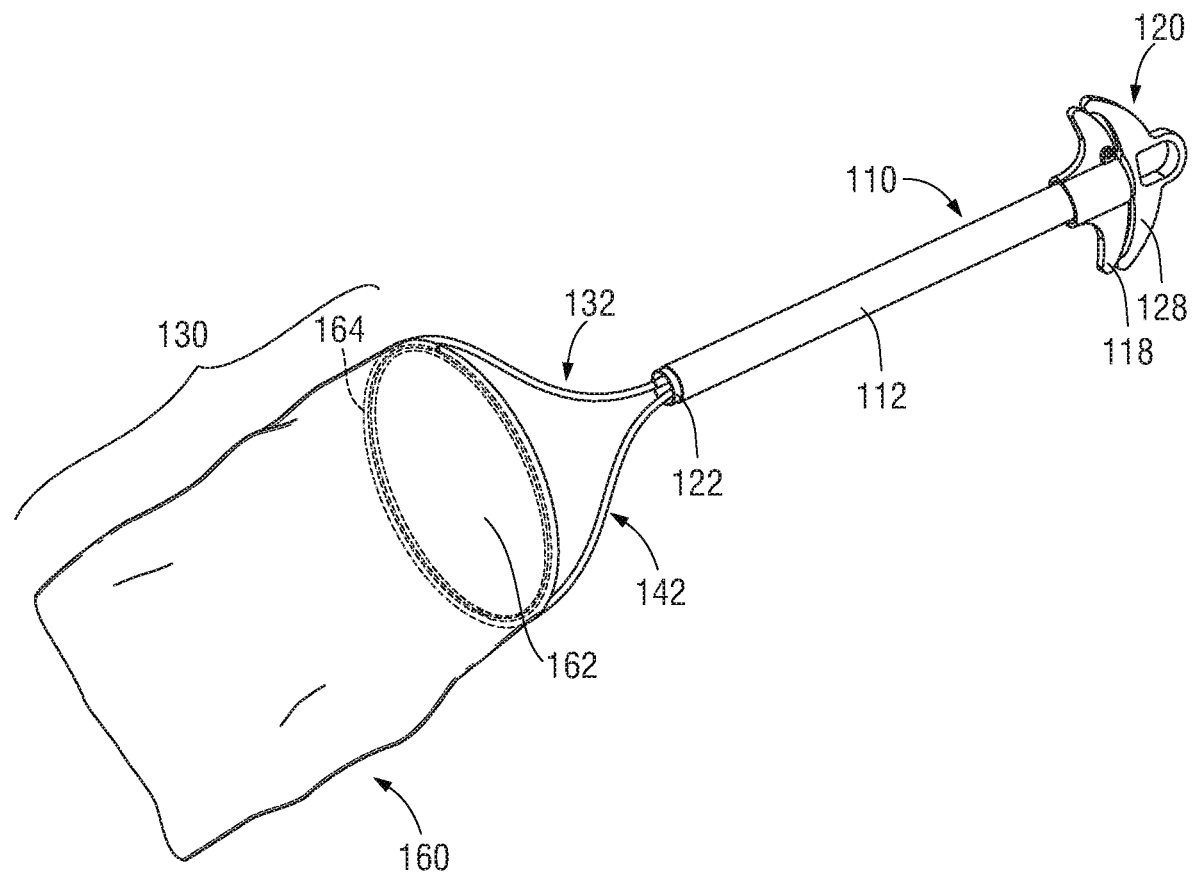
FIG. 2 is a perspective view of the tissue specimen retrieval device of FIG. 1, disposed in a deployed position.

Turning to FIGS. 1-2, a tissue specimen retrieval device provided in accordance with the present disclosure is shown generally identified by reference numeral 100. Tissue specimen retrieval device 100 includes a first body 110, a second body 120, and an end effector assembly 130 including a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2), wherein end effector assembly 130 extends distally from first shaft 112. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2) to move tissue specimen retrieval device 100 from the retracted position (FIG. 1), wherein end effector assembly 130 is disposed within first shaft 112, to the deployed position (FIG. 2), wherein end effector assembly 130 extends distally from first shaft 112.

Figure 3:
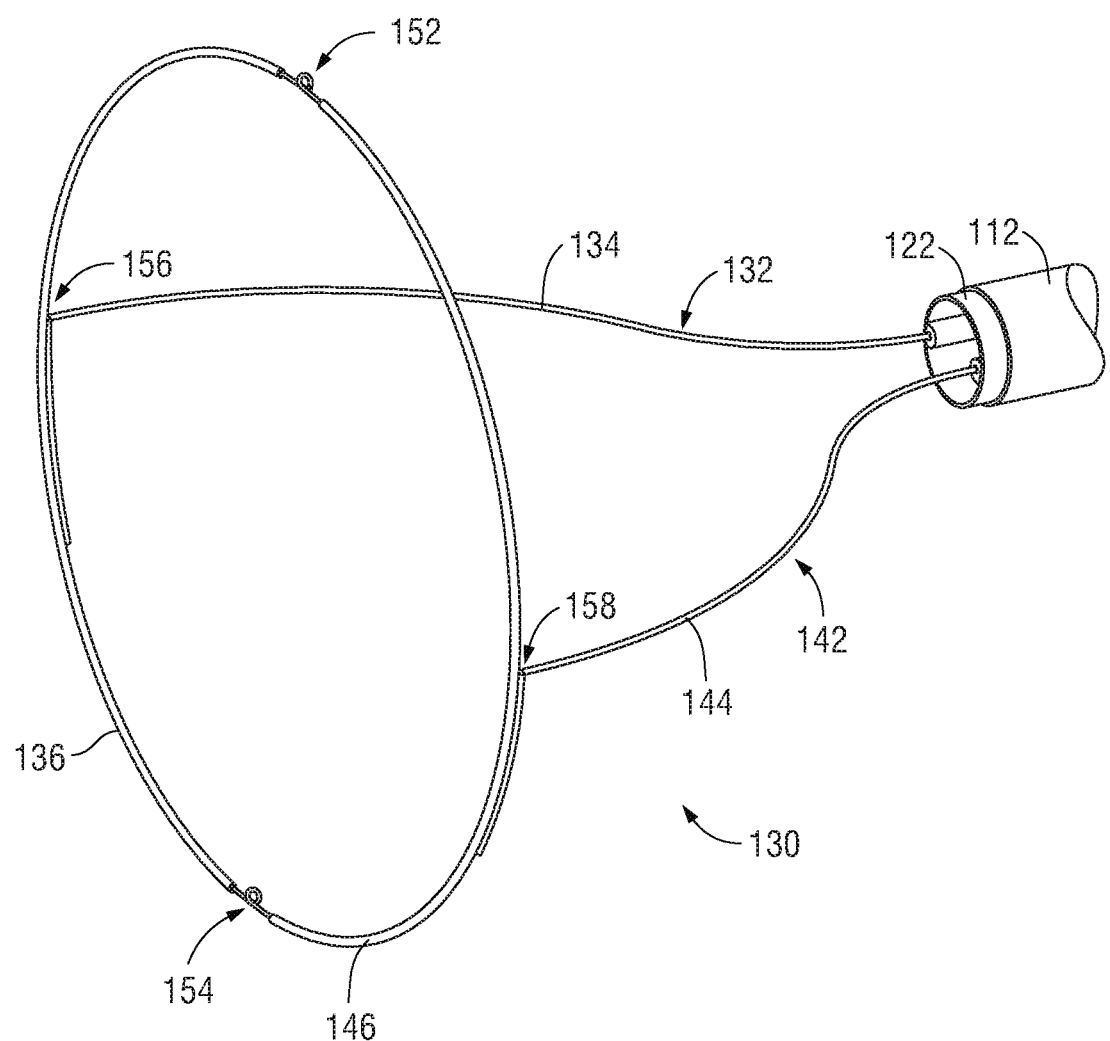
FIG. 3 is an enlarged, perspective view of the end effector assembly of the tissue specimen retrieval device of FIG. 1 with the specimen bag removed therefrom.

Referring to FIGS. 2 and 3, end effector assembly 130, as noted above, is supported at distal end portion 126 of second shaft 122. End effector assembly 130, more specifically, includes first and second arms 132, 142 extending distally from distal end portion 126 of second shaft 122 and a specimen bag 160 supported by and depending from first and second arms 132, 134. Each of first and second arms 132, 142 includes a proximal segment 134, 144 engaged with and extending distally from distal end portion 126 of second shaft 122, and a distal segment 136, 146 coupled to the respective proximal segment 134, 144 and extending distally therefrom.

Proximal segments 134, 144 of arms 132, 142, respectively, are substantially co-planar with one another so as to define a plane bisecting proximal segments 134 and 144, and are formed from resiliently flexible material, e.g., nitinol tubing, that biases proximal segments 134, 144 towards a first expanded position. Proximal segments 134, 144 each define, in the first expanded position, a curvature along at least a portion of the length thereof such that the proximal portions of proximal segments 134, 144 are relatively closer to one another and the distal portions of proximal segments 134, 144 are relatively father apart from one another.

Proximal segments 134, 144 of arms 132, 142, respectively, may be resiliently flexed from the first expanded position towards a first collapsed position, wherein the curvatures of proximal segments 134, 144 are at least partially eliminated and the distal portions of proximal segments 134, 144 are moved closer to one another, e.g., such that proximal segments 134, 144 are moved towards a substantially parallel orientation. Proximal segments 134, 144 are configured to resiliently flex within the plane defined thereby such that proximal segments 134, 144 remain substantially co-planar with one another in each of and during movement between the first expanded and first collapsed positions.

As an alternative or in addition to curved and/or resilient flexible configurations, proximal segments 134, 144 may define linear and/or substantially rigid configurations including one or more joints therealong to enable movement of proximal segments 134, 144 or portions thereof between the first expanded and first collapsed positions.

Distal segments 136, 146 of arms 132, 142, respectively, are substantially co-planar with one another so as to define a plane bisecting distal segments 136 and 146. Distal segments 136, 146 define curved configurations and are oriented relative to one another to cooperatively define a substantially oval-shaped configuration. Distal segments 136, 146 are formed from resiliently flexible material, e.g., nitinol tubing, that biases distal segments 136, 146 to a second expanded position, wherein distal segments 136, 146 cooperate to define a more-circular configuration.

Distal segments 136, 146 of arms 132, 142, respectively, are coupled to one another at first ends thereof via a first joint 152 and at second, opposite ends thereof via a second joint 154. In embodiments, first and second joints 152, 154 provide a bias that contributes to biasing distal segments 136, 146 towards the second expanded position; in other embodiments, the bias towards the second expanded position is provided by distal segments 136, 146 themselves without substantial bias imparted by first and second joints 152, 154. In either configuration, joints 152, 154 and distal segments 136, 146 are configured to move against the bias(es) such that distal segments 136, 146 are moved from the second expanded position, wherein distal segments 136, 146 cooperate to define the more-circular configuration, to a second collapsed position, wherein distal segments 136, 146 cooperate to define an elongated, oval-shaped configuration. Distal segments 136, 146 are configured to resiliently flex, and first and second joints 152, 154 are configured to move, within the plane defined by distal segments 136, 146, e.g., such that distal segments 136, 146 remain substantially co-planar with one another in each of and during movement between the second expanded and second collapsed positions. First and joints 152, 154 may be hinge joints (living or multi-component hinges), pivot joints, torsion spring joints (similarly as detailed below), or other suitable joints.

As an alternative or in addition to distal segments 136, 146 cooperating to define an oval-shaped configuration and/or being resiliently flexible, distal segments 136, 146 may define linear and/or substantially rigid configurations including a plurality of joints, e.g., two joints, four joints, five joints, etc., defining a polygonal configuration, while still being movable between the second expanded position and the second collapsed position.

With reference to FIG. 2, distal segments 136, 146 support specimen bag 160 thereon with specimen bag 160 depending therefrom. Specimen bag 160 may be formed from any suitable bio-compatible material (or materials), e.g., ripstop nylon, configured to retain a tissue specimen therein. Specimen bag 160 defines at least one opening, e.g., open end 162 thereof, for receipt of a tissue specimen therein. Specimen bag 160 may include one or more channels 164 formed about at least a portion of the perimeter of open end 162 thereof for retaining distal segments 136, 146 of arms 132, 142, respectively, therein to support specimen bag 160 on distal segments 136, 146. Alternatively, open end 162 of specimen bag 160 may be welded, adhered, or otherwise affixed to or about distal segments 136, 146 to support specimen bag 160 thereon.

The one or more openings of specimen bag 160, e.g., open end 162, may include a cinch cord (not shown) disposed thereabout to enable selective closure of the opening. Specimen bag 160 may be disengaged from distal segments 136, 146 upon cinching closed open end 162 of specimen bag 160, retraction of end effector assembly 130 back towards the retracted position (FIG. 1), using a separate instrument, e.g., grasping device, and/or in any other suitable manner Turning again to FIGS. 2 and 3, distal segments 136, 146 of arms 132, 142 are coupled to respective proximal segments 134, 144 of arms 132, 142 via third and fourth joints 156, 158, respectively, to enable a collapsing of end effector assembly 130 wherein distal segments 136, 146 are collapsed onto to proximal segments 134, 144. Third and fourth joints 156, 158 may be hinge joints (living or multi-component hinges), pivot joints, torsion spring joints (similarly as detailed below), or other suitable joints. Third and fourth joints 156, 158, more specifically, enable collapsing of distal segments 136, 146 relative to proximal segments 134, 144 from a third expanded position (see FIG. 4A), wherein the planes defined by distal segments 136, 146 and proximal segments 134, 144 are disposed in a first orientation relative to one another, to a third collapsed position (see FIG. 4B), wherein the planes defined by distal segments are disposed in a second orientation relative to one another. Third and fourth joints 156, 158 are configured to bias distal segments 136, 146 towards the third expanded position relative to proximal segments 134, 144, wherein the planes defined thereby are disposed in the first orientation, although other configurations are also contemplated.

In embodiments, in the third expanded position, corresponding to the first orientation of the planes defined by distal segments 136, 146 and proximal segments 134, 144, the planes are disposed in substantially perpendicular orientation relative to one another; in other embodiments, the planes define an angle therebetween of approximately 45 degrees to approximately 120 degrees; in still other embodiments, the planes define an angle therebetween of approximately 60 degrees to approximately 105 degrees; and in yet other embodiments, the planes define an angle therebetween of approximately 75 degrees to approximately 90 degrees.

In embodiments, in the third collapsed position, corresponding to the second orientation of the planes defined by distal segments 136, 146 and proximal segments 134, 144, the planes are disposed in substantially parallel orientation relative to one another; in other embodiments, the planes define an angle therebetween of approximately 0 degrees to approximately 15 degrees; in still other embodiments, the planes define an angle therebetween of approximately 0 degrees to approximately 10 degrees; and in yet other embodiments, the planes define an angle therebetween of approximately 0 degrees to approximately 5 degrees.

Turning back to FIGS. 1 and 2, in the retracted position of tissue specimen retrieval device 100 (FIG. 1), as noted above, end effector assembly 130 is disposed within first shaft 112 of first body 110. In order to fit end effector assembly 130 within first shaft 112 in the retracted position of tissue specimen retrieval device 100 (FIG. 1), two collapses of end effector assembly 130 are provided, as detailed below. Although described herein in terms of a first collapse followed by a second collapse, the present disclosure also contemplates that the first collapse follows the second collapses, or that at least portions of the first and second collapses are effected substantially simultaneously.

Figure 4A:
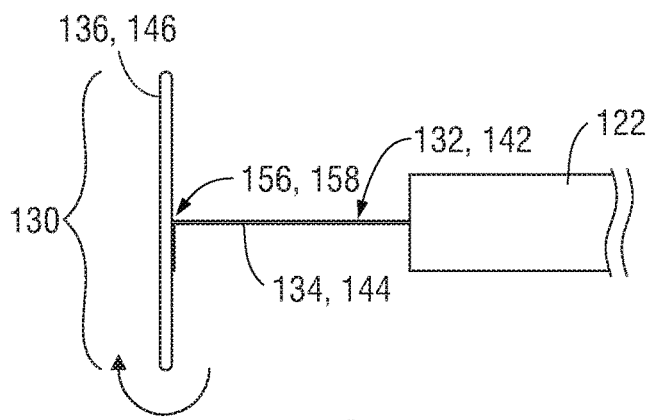
FIGS. 4A and 4B are side views of the end effector assembly of the tissue specimen retrieval device of FIG. 1 illustrating a first collapsing of the end effector assembly.
Figure 4B:
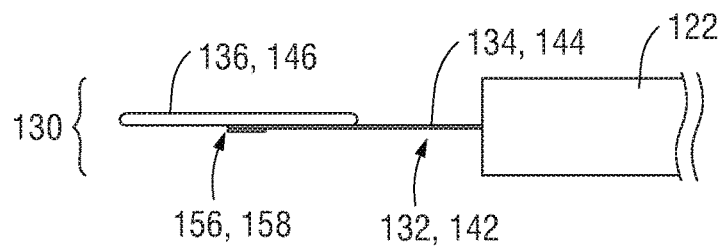

Referring to FIGS. 4A and 4B, the first collapse corresponds to the movement of distal segments 136, 146 of arms 132, 142 about third and fourth joints 156, 158, respectively, and relative to respective proximal segments 134, 144 from the third expanded position to the third collapsed position, as detailed above. This movement of distal segments 136, 146 about third and fourth joints 156, 158 to effect the first collapse occurs via relative movement of the planes defined by proximal segments 134, 144 and distal segments 136, 146, e.g., the plane defined by distal segments 136, 146 is moved relative to the plane defined by proximal segments 134, 144 during the first collapse.

Figure 5A:
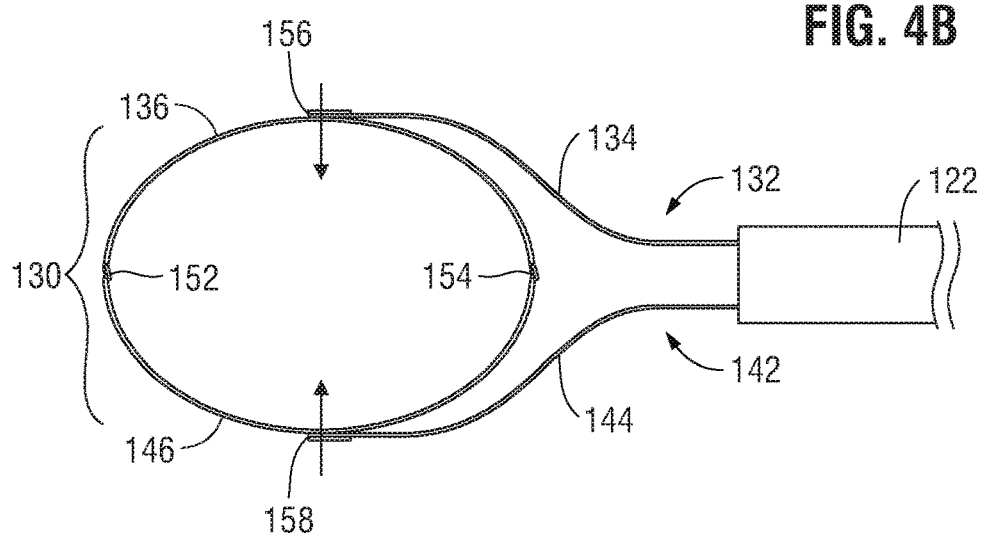
FIGS. 5A and 5B are top views of the end effector assembly of the tissue specimen retrieval device of FIG. 1 illustrating a second collapsing of the end effector assembly.
Figure 5B:
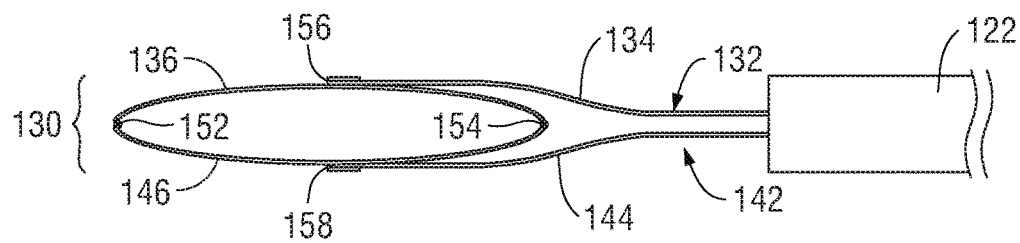

The second collapse, illustrated in FIGS. 5A and 5B, is a compound collapse corresponding to the flexion and movement about joints 152, 152 of distal segments 136, 146 of arms 132, 142, respectively, from the second expanded position to the second collapsed position, as detailed above, as well as flexion of proximal segments 134, 144 of arms 132, 142 from the first expanded position to the first collapsed position, as also detailed above. These movements corresponding to the second collapse occur within the planes defined by proximal segments 134, 144 and distal segments 136, 146, respectively such that the planes defined by proximal segments 134, 144 and distal segments 136, 146 remain substantially stationary relative to one another during the second collapse.

With additional reference to FIGS. 1 and 2, once the first and second collapses are effected, as detailed above, specimen bag 160 may be folded, twisted, wrapped, rolled, and/or otherwise manipulated relative to arms 132, 142 and, thereafter, second shaft 122 may be pulled proximally relative to first shaft 112, e.g., via moving second handle 128 away from first handle 118, thereby drawing end effector 130 into first shaft 112 to the retracted position. As an alternative to initially manipulating specimen bag 160 relative to arms 132, 142 before drawing end effector 130 into first shaft 112, arms 132, 142 of end effector assembly 130 may instead be at least partially drawn into first shaft 112 followed by manipulating specimen bag 160 to fit within first shaft 112. In other embodiments, rather than effecting the first and second collapses in the deployed position and the retracting end effector assembly 130 proximally into first shaft 130, end effector assembly 130, after the first and second collapses are effected, may be inserted through the proximal end portion 114 of first shaft 112 and moved therethrough to the retracted position, e.g., via manipulating second handle 128. Other suitable configurations for loading end effector assembly 130 within first shaft 112 are also contemplated. Regardless of the loading configuration, once loaded within first shaft 112 in the retracted position, the first and second collapses of arms 132, 142 of end effector assembly 130 are maintained against the biases thereof via the internal spatial constraints of first shaft 112.

Continuing with reference to FIGS. 1 and 2, with end effector assembly 130 loaded within first shaft 112 and tissue specimen retrieval device 100 disposed in the retracted position (FIG. 1), tissue specimen retrieval device 100 is ready for use. More specifically, tissue specimen retrieval device 100 may be inserted into an internal surgical site, e.g., through a suitable access device (not shown), and thereafter moved from the retracted position to he deployed position, e.g., via grasping second handle 128 and moving second handle 118 towards first handle 118.

As end effector assembly 130 is deployed from first shaft 112 and, thus, is no longer constrained by first shaft, proximal segments 134, 144 of arms 132, 142 are returned from the first collapsed position to the first expanded position, distal segments 136, 146 of arms 132, 142 are returned from the second collapsed position back to the second expanded position, and distal segments 136, 146 are returned relative to proximal segments 134, 144 from the third collapsed position to the third expanded position. The return to the first, second, and third expanded positions may occur in any order and/or portions thereof may occur substantially simultaneously. Further, upon return to the first, second, and/or third expanded positions, specimen bag 160 is unfurled and open end 162 thereof presented to facilitate insertion of a tissue specimen therein during use.

Figure 6A:
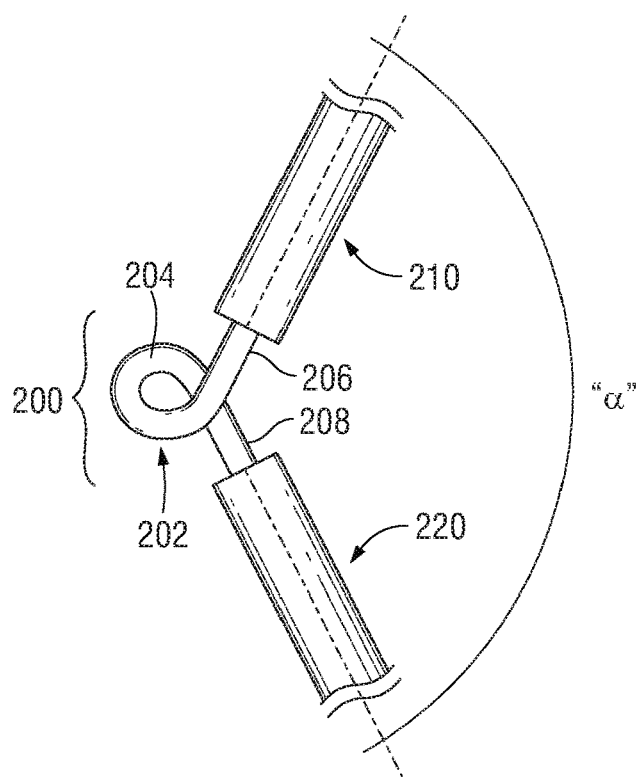
FIG. 6A is a side view of a joint of the end effector assembly of the tissue specimen retrieval device of FIG. 1, disposed in an at-rest position.
Figure 6B:
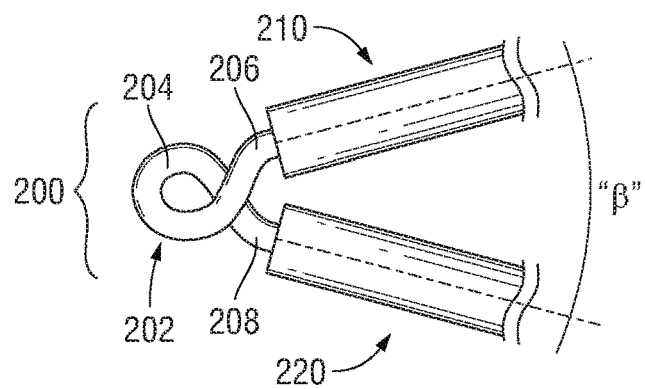
FIG. 6B is a side view of the joint of FIG. 6A, disposed in a loaded position.
Figure 7:
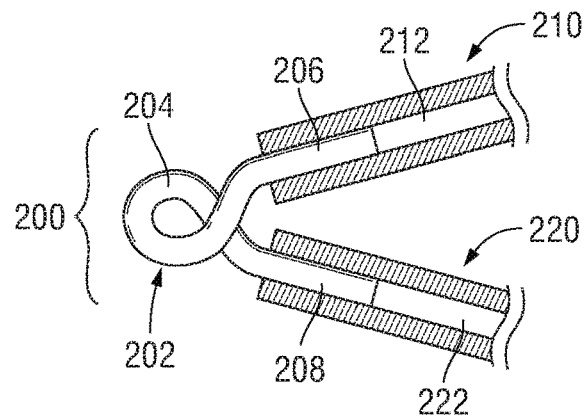
FIG. 7 is a transverse, cross-sectional view of the joint of FIGS. 6A and 6B, disposed in the loaded position.

Turning now to FIGS. 6A-6B and 7, a torsion spring joint provided in accordance with the present disclosure is shown generally identified by reference numeral 200 including a torsion spring 202 operably coupling first and second tube portions 210, 220, respectively, with one another. Torsion spring joint 200 may be utilized as one or more of joints 152, 154, 156, 158 and, thus, first and second tube portions 210, 220 may be the first ends of distal segments 136, 146, the second ends of distal segments 136, 146, the coupled portions of proximal and distal segments 134, 136 of arm 132, and/or the coupled portions of proximal and distal segments 144, 146 of arm 142 (see FIG. 3). However, torsion spring joint 200 may additionally or alternatively be utilized to operably couple first and second tube portions 210, 220, respectively, of any other suitable end effector assembly to facilitate movement thereof between at least one expanded position and at least one collapsed position.

Torsion spring joint 200 includes a torsion spring 202 having a body 204 and first and second legs 206, 208 extending from body 204. Body 204 includes one or more loops defining a coil, while legs 206, 208 extend in substantially linear fashion from body 204. In an at-rest position of body 204, legs 206, 208 extend from body 204 to define a first angle "α" therebetween (FIG. 6A). Moving legs 206, 208 towards or away from one another from the at-rest position to a loaded position, e.g., wherein legs 206, 208 define a second angle "β" therebetween (FIG. 6B), further coils body 204, thereby loading or tensioning torsion spring 202. Thus, in the absence of sufficient force to retain legs 206, 208 in the loaded position, the tension built up in body 204 urges legs 206, 208 back towards the at-rest position. Legs 206, 208 may be configured to move through a range of motion of up to approximately 180 degrees, e.g., wherein first angle "α" is approximately 180 degrees and second angle "β" is approximately 0 degrees, although other ranges of motion and/or maximum and minimum range angles are also contemplated.

As illustrated in FIG. 7, first and second legs 206, 208 of torsion spring 202 are at least partially received within internal lumens 212, 222 defined with first and second tube portions 210, 220, respectively. Accordingly, and with additional reference to FIGS. 6A and 6B, moving first and second tube portion 210, 220 towards one another, e.g., from an expanded position to a collapsed position, moves legs 206, 208, respectively, towards one another from the at-rest position to the loaded position, thereby tensioning body 204. Accordingly, without sufficient force to maintain first and second tube portions 210, 220 in the collapsed position, the tension built up in body 204 urges legs 206, 208 back towards the at-rest position and, thus, first and second tube portions 210, 220 back to the expanded position. That is, torsion spring 202 biases first and second tube portions 210, 220 towards the expanded position.

First and second legs 206, 208 of torsion spring 202 may be maintained within internal lumens 212, 222 of first and second tube portions 210, 220, respectively, via friction-fitting, welding, adhesive, other suitable engagement or via an external constraint such as, for example, heat shrink disposed about torsion spring 202 and first and second tube portions 210, 220, positioning torsion spring 202 and first and second tube portions 210, 220 within a channel of a specimen bag, e.g., channel 164 of specimen bag 160, forming a portion of a specimen bag about torsion spring 202 and first and second tube portions 210, 220, e.g., forming a channel 164 of specimen bag 160 retaining torsion spring 202 and first and second tube portions 210, 220 therein, or in any other suitable manner.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of a tissue specimen retrieval device, the end effector assembly comprising:
    a first arm including a first proximal segment and a first distal segment, the first distal segment including first and second end portions;
    a second arm including a second proximal segment and a second distal segment, the second distal segment including first and second end portions;
    a first joint directly coupling the first end portions of the first and second distal segments;
    a second joint directly coupling the second end portions of the first and second distal segments;
    a third joint directly coupling the first proximal and first distal segments; and
    a fourth joint directly coupling the second proximal and second distal segments,
    wherein the first and second distal segments are movable relative to one another about the first and second joints, and wherein the first and second distal segments are movable relative to the first and second proximal segments about the third and fourth joints.

2. The end effector assembly according to claim 1, further comprising a tissue specimen bag supported on the first and second distal segments.

3. The end effector assembly according to claim 1, wherein the first and second proximal segments are substantially co-planar to thereby define a first plane and wherein the first and second distal segments are substantially co-planar to thereby define a second plane.

4. The end effector assembly according to claim 3, wherein movement of the first and second distal segments relative to the first and second proximal segments about the third and fourth joints moves the first and second planes relative to one another.

5. The end effector assembly according to claim 3, wherein the first and second proximal segments are configured to flex relative to one another.

6. The end effector assembly according to claim 5, wherein the first and second planes remain relatively stationary during flexion of the first and second proximal segments relative to one another.

7. The end effector assembly according to claim 3, wherein the first and second planes remain relatively stationary during movement of the first and second distal segments relative to one another about the first and second joints.

8. The end effector assembly according to claim 1, wherein at least one of the first, second, third, or fourth joints includes a torsion spring.

9. The end effector assembly according to claim 8, wherein the torsion spring includes a body and first and second legs extending from the body, the first and second legs configured to engage first and second tube portions such that movement of the first and second tube portions relative to one another tensions or un-tensions the body.

10. A tissue specimen retrieval device, comprising:
a first shaft;
a second shaft telescopically movable relative to the first shaft, the second shaft supporting an end effector assembly at a distal end portion thereof and movable relative to the first shaft between a retracted position, wherein the end effector assembly is disposed within the first shaft, and a deployed position, wherein the end effector assembly extends distally from the first shaft, the end effector assembly including:
a first arm including a first proximal segment and a first distal segment, the first distal segment including first and second end portions;
a second arm including a second proximal segment and a second distal segment, the second distal segment including first and second end portions;
a first joint directly coupling the first end portions of the first and second distal segments;
a second joint directly coupling the second end portions of the first and second distal segments;
a third joint directly coupling the first proximal and first distal segments; and
a fourth joint directly coupling the second proximal and second distal segments,
wherein, upon movement of the second shaft to the deployed position, the first and second distal segments are moved relative to one another about the first and second joints, and the first and second distal segments are movable relative to the first and second proximal segments about the third and fourth joints.

11. The tissue specimen retrieval device according to claim 10, further comprising a first handle disposed at a proximal end portion of the first shaft and a second handle disposed at a proximal end portion of the second handle, wherein the first and second handles are relatively movable to move the second shaft between the retracted and deployed positions.

12. The tissue specimen retrieval device according to claim 10, further comprising a tissue specimen bag supported on the first and second distal segments.

13. The tissue specimen retrieval device according to claim 12, wherein, in the retracted position, the tissue specimen bag is disposed within the first shaft.

14. The tissue specimen retrieval device according to claim 10, wherein the first and second proximal segments are substantially co-planar to thereby define a first plane and wherein the first and second distal segments are substantially co-planar to thereby define a second plane.

15. The tissue specimen retrieval device according to claim 14, wherein movement of the first and second distal segments relative to the first and second proximal segments about the third and fourth joints moves the first and second planes relative to one another.

16. The tissue specimen retrieval device according to claim 14, wherein the first and second proximal segments are configured to flex relative to one another.

17. The tissue specimen retrieval device according to claim 16, wherein the first and second planes remain relatively stationary during flexion of the first and second proximal segments relative to one another.

18. The tissue specimen retrieval device according to claim 14, wherein the first and second planes remain relatively stationary during movement of the first and second distal segments relative to one another about the first and second joints.

19. The tissue specimen retrieval device according to claim 10, wherein at least one of the first, second, third, or fourth joints includes a torsion spring.

20. The tissue specimen retrieval device according to claim 19, wherein the torsion spring includes a body and first and second legs extending from the body, the first and second legs configured to engage first and second tube portions such that movement of the first and second tube portions relative to one another tensions or un-tensions the body.

* * * * *